United States Patent [19]

Hurley et al.

[11] Patent Number: 4,918,178

[45] Date of Patent: Apr. 17, 1990

[54] TEST FOR JOHNE'S DISEASE

[75] Inventors: Sarah S. Hurley, Stoughton; Gary A. Splitter, Brooklyn; Rodney A. Welch, Madison, all of Wis.

[73] Assignee: Wisconsin Alumni Research Foundation, Madison, Wis.

[21] Appl. No.: 112,179

[22] Filed: Oct. 22, 1987

[51] Int. Cl.⁴ ................. C07H 21/04; C12N 15/00; C12Q 1/68; C12R 1/32

[52] U.S. Cl. ........................ 536/27; 435/6; 435/863; 436/501; 436/811; 935/78

[58] Field of Search ............ 435/6, 863; 436/501, 436/811; 536/27; 935/78

[56] References Cited

U.S. PATENT DOCUMENTS

4,358,535 11/1982 Falkow et al. ................. 435/5
4,362,867 12/1982 Paddock ........................ 536/27

FOREIGN PATENT DOCUMENTS

205662 1/1988 European Pat. Off. .
285439 10/1988 European Pat. Off. .
288306 10/1988 European Pat. Off. .

OTHER PUBLICATIONS

J. McFadden et al., J. Clin. Microb., 25, 796–801, (May 1987).
J. McFadden et al., Biochem. Soc. Trans., 15, 547–548, (1987).
L. Trnka et al., Experentia, 24, 1109–1110, (1968).
H. Yoshimura et al., Abstracts of the Annual Meeting of the American Society of Microbiol., vol. 85, p. 103, Abstract U 31, (1985).
L. Cooke, Agricultural Research, 35, 4, (Oct. 1987).
S. Hurley et al., J. Clin. Microbio., 25, 2227–2229, (Nov. 1987).
S. Hurley et al., Int. J. Sys. Bacteriol., 38, 143–146, (1988).
Four pages of advertisement from Biospec Products, undated, entitled "The Bead-Beater", (prior art).
Baess, I. and M. W. Bentzon, Acta. Path. Microbiol. Scand., § B, 86, 71–76, (1978).
Clark-Curtiss, J. et al., J. Bacteriol., 161, 1093–1102, (1985).
Thole, J. et al., Infect. and Immun., 50, 800–806, (1985).
Moseley, S. et al., J. Infect. Diseases, 145, 863–869, (1982).
Legerski, R. et al., J. Mol. Biol., 181, 297–312, (1985).
*M13 Cloning and Sequencing Handbook*, Amersham Corp., pp. 25–29, (Arlington, Heights, Ill.).
Thomas, P., P.N.A.S. U.S.A., 77, 5201–5205, (1980).
Rigby, P., J. Mol. Biol., 113, 237–251, (1977).
Southern, E., J. Mol. Biol., 98, 503–517, (1975).
Maniatis, T., P.N.A.S. U.S.A., 72, 1184–1188, (1975).
Darby, G. et al., J. Bact., 103, 159–165, (1970).
Hill, E. et al., J. Bact., 112, 1033–1039, (1972).

*Primary Examiner*—Amelia Burgess Yarbrough
*Assistant Examiner*—Ardin H. Marschel
*Attorney, Agent, or Firm*—Quarles & Brady

[57] ABSTRACT

A test to diagnose the presence of Johne's disease is disclosed. In one aspect it involves using a DNA segment that will hybridize to *M. paratuberculosis* but not to other bacteria typically found in bovine feces. Another aspect of the invention is providing a process for breaking the cell wall of mycobacteria using dense beads in the presence of phenol.

4 Claims, No Drawings

TEST FOR JOHNE'S DISEASE

This invention was made with United States government support awarded by the United States Department of Agriculture (USDA), Grant No.: 86-CRSE-2-2863. The United States Government has certain rights in this invention.

The present invention relates to a diagnostic test for Johne's disease and to compounds useful in connection with such tests. More particularly it relates to a labelled DNA hybridization probe that has specificity for *M. paratuberculosis* (the bacteria that causes the disease), and to an improved means of preparing fecal samples containing the bacteria so that the probe can be used on a routine basis.

BACKGROUND OF THE INVENTION

Johne's disease is a chronic, debilitating disease of ruminants (e.g. cows) characterized by diarrhea which usually leads to death. Infected cattle may not exhibit debilitating symptoms for a long period after infection. By the time the symptoms are evident, three to four years of investment in the cattle has been wasted. Further, over that period other cattle and pasture areas can be exposed to the disease. A test that could be performed within a week's time, that is relatively inexpensive to perform, that would be specific for Johne's disease, and that would be sensitive enough to detect the disease in its early stages using fecal samples, would be a useful tool in herd management, regulatory medicine, and other aspects of work with Johne's disease.

The art has previously developed DNA hybridization probes for the identification of some other *Mycobacterium* (e.g. *leprae* and *bovis*). The hybridization technique depends upon finding DNA sequences from the bacteria that will stick (hybridize) to the bacterial DNA, are short enough to be cloned, and are unique enough not to hybridize to DNA from other bacteria. One then labels the probe with a colorimetric or radioactive marker, and then uses the probe to locate the DNA in a sample.

Because of the high degree of homology between *M. bovis*, *M. phlei* and *M. scrofulaceum* on the one hand and *M. paratuberculosis* on the other, and the presence of *M. bovis*, *M. phlei*, and/or *M. scrofulaceum* in some bovine fecal samples, DNA probe hybridization techniques did not appear to be well suited to be used in a Johne's test (because of the lack of specificity of most DNA sequences in these bacteria). Moreover, hybridizing Mycobacterium DNA has in the past been hindered by the laborious procedures required to break open the bacterial cell to obtain access to the cell DNA (in order to permit use of hybridization techniques). In this regard, *M. paratuberculosis* has a very thick lipid-rich cell wall. This, and slow replication of this mycobacteria, can make use of conventional chemical cell wall disruption techniques especially tedious. For example, weakening bacterial cell walls by growth for several generations in the presence of 100 to 200 mM glycine, and lysis achieved by lysozyme, proteinase K, and sodium dodecyl sulfate treatment has been tried. However, such procedures can take days.

Conventional mechanical lysis procedures, such as the French press, the Hughes press, and the Ribi pressure cell, take less time than chemical methods (minutes compared with hours or days). They use pressure for rupture of the bacteria. Briefly, bacteria are placed in a chamber where a piston compresses the atmosphere of the chamber (80,000 lbs./square inch). The pressure is then released through a small super cooled valve and the sudden pressure change ruptures the cells. However, growing the cell cultures and achieving the appropriate concentration and volume can be time-consuming. In addition, impurities, such as those that might be present in feces, can damage the equipment used in these techniques.

SUMMARY OF THE INVENTION

In one aspect, the present invention provides an assay to detect the presence of an *M. paratuberculosis* cell in a sample of a ruminant's feces. One first breaks open the cell's wall in a bead type beater by causing a bead to bounce against the cell in a liquid in which the feces has been placed. After that, one tests for the presence of *M. paratuberculosis* DNA using a nucleotide containing segment capable of distinguishing *M. paratuberculosis* from *M. bovis*, *M. phlei*, and *M. scrofulaceum* in a hybridization test. In a preferred assay, the nucleotide containing segment is DNA, the liquid contains phenol at the time the *M. paratuberculosis* cell wall is being broken open in the bead beater, and the bead has a density of at least $3g/cm^3$. The cell wall disruption technique also has proved useful to disrupt the cell wall of other Mycobacteria.

In another form of the invention, there is provided a nucleotide containing segment capable of distinguishing *M. paratuberculosis* from *M. bovis*, *M. phlei*, and *M. scrofulaceum* using a hybridization test. Preferably, the segment is DNA which is labelled with an indicator or marker (radioactive or color) which enables it to be easily spotted by the technician.

Through the use of several clever screening techniques and then random luck, the applicants were surprisingly able to isolate a DNA sequence that is sufficiently unique that it can be used to distinguish *M. paratuberculosis* from *M. bovis*, *M. phlei*, and *M. scrofulaceum* in fecal samples. Further, they have discovered that through the use of a bead beater/phenol system, crude fecal samples can be efficiently processed to prepare the sample's DNA for probe analysis.

The objects of the invention therefore include providing a nucleotide containing probe and assay of the above kind to enable one to test for Johne's disease.

Another object is to provide an assay of the above kind which is simple, relatively inexpensive, and easy to perform.

Still other objects and advantages of the present invention will be apparent from the description which follows.

DESCRIPTION OF THE PREFERRED EMBODIMENTS

It should be understood that the description of the preferred embodiments are merely examples of the invention. They are not intended to represent the full scope of the invention. Rather, the claims should be looked to in order to determine the full scope of the invention.

Materials

Mycobacterial strains and sources were as follows: *M. paratuberculosis* ATCC 19698 Trudeau Mycobacterial Culture Collection, National Jewish Hospital, Denver, Colo. [TMC] and NADC 19698 and Strain 18 (National Animal Disease Center (NADC) Denver, Colo.);

*M. avium* TMC 715 serotype 2 (bovine) (TMC) and TMC 702 serotype 6 (avian), TMC 801 serotype 2 (avian), mycobactin dep 5, mycobactin dep 7, and mycobactin dep 8 (NADC); wood pigeon bacillus (M. F. Thorel) (NADC); *M. intracellulare* TMC 1479 serotype 9 (bovine) (TMC) and TMC 1472 serotype 6 (porcine) (NADC); *M. scrofulaceum* TMC 1320 serotype 43 (human) (TMC) and Anderson serotype 43, EWO407 serotype 42, CDC 1198 serotype 42, Cardiff serotype 41, Bridge serotype 41 (human), and M150 serotype 43 (National Jewish Hospital); *M. bovis* TMC 410 (bovine) (TMC); *M. fortuitum* TMC 1529 fortuitum 2 (human) (NADC); and *M. phlei* TMC 1548 (hay) (TMC) and NADC not typed (NADC).

Phage M13 (a vector) was obtained from New England Biolabs, Beverly, Mass. The host, *E. coli* JM101, was also acquired from New England Biolabs.

Isolation of the Probe

Fragments of *M. paratuberculosis* DNA were generated with restriction enzyme Sau3A under standard restriction enzyme conditions. The fragments of DNA were inserted into phage vector M13 using procedures analogous to R. Legerski et al., 181 J. Mol. Biol. 297–312 (1985). See also T. Maniatis et al., Molecular Cloning-A Laboratory Cloning Manual, Cold Spring Harbor (1982). The disclosure of these articles and of all other articles recited herein are incorporated by reference as if fully set forth herein. The procedure for transfecting a host (*E. coli* JM101) with the M13 vector was as stated in the M13 Cloning & Sequencing Handbook, Amersham Corp. 25–29, Arlington Heights, Ill. The use of an M13 vector offers the advantage of being able to obtain single-stranded DNA circular forms of the insert by harvesting the insert containing phage DNA viral particles extruded into the media by infected *E. coli* JM101 clones.

The insert containing phage DNA's from these clones were pooled and hybridized against *M. avium* Sau3A genomic DNA fragments which were bound to nitrocellulose (using techniques analogous to P. Thomas, 77 P.N.A.S. U.S.A. 5201–5205 (1980). The idea was that only sequences with little or no homology to *M. avium* would stay in solution, while those with greater homology will stick to the paper at one of several passes. This enriches for good probe candidates.

The unhybridized phage DNA's remaining in solution were collected, used to reinfect *E. coli* JM101, then randomly used to generate more clones. These clones were screened by hybridizing identical dot blots of individual phage supernates against radiolabelled genomic DNA from *M. avium* and *M. paratuberculosis*.

Several clones bound with greater avidity to *M. paratuberculosis* than to *M. avium* (and not to *M. bovis*, *M. phlei* or *M. scrofulaceum*). This was confirmed when the clones were radiolabelled and hybridized individually against a Southern blot of the particular DNA. For hybridization procedures, See P. Rigby, 113 J. Mol. Biol. 237–251 (1977); E. Southern, 98 J. Mol. Biol. 503–517 (1975). Hybridization and washes were performed under high stringency with 65° C. with 50% formamide.

The best probe found to date is the sequence currently deposited with the American Type Culture Collection, Rockville, Md., as ATCC #40380. It is incorporated in double stranded circular M13 phage DNA stored in cesium chloride. This deposit will be made available to the extent required under applicable patent laws. Such availability is not intended as a license. It will be appreciated that by using this probe as a hybridization screen, or sequencing it, other DNA fragments (and perhaps RNA or nucleotide containing variant fragments) having suitable characteristics may also be isolated or synthesized.

Labelling the Probe

To radiolabel the DNA probe, one uses alpha $^{32}$P deoxy nucleotide triphosphate (New England Nuclear Co., Boston) to perform nick translation by techniques analogous to those described in T. Maniatis, 72 P.N.A.S. U.S.A. 1184–1188 (1975). One can also use a standard commercial protocol such as that of Bethesda Research Laboratories. As an alternative, biotin-avidin nick translation (biotin-7-dATP or biotin-11-dUTP) using a standard commercial protocol can be used to create a color marker on the probe.

Cell Disruption

To disrupt the cell wall, we used the Mini-Beadbeater #3110BX produced by Biospec Products, Bartlesville, Okla. It holds a tube horizontally and then shakes the tube back and forth on its longitudinal axis with beater balls and liquid inside the tube. The preferred balls are zirconium oxide which are of a density of at least 3g/cm$^3$. The preferred density for the balls is at least 5.5g/cm$^3$.

As an initial test, cultures of *M. paratuberculosis* grown in Middlebrook 7H9 broth were pelleted, and the cell pellet was suspended in sufficient 1 M Tris EDTA (TE) buffer (pH 8.0) to make a 50% cell suspension. The suspension was pipetted in 500- to 600-µl aliquots into 1.5-ml screwcap polypropylene tubes (Walter Sarstedt, Inc.). A volume of TE-saturated phenol equal to the volume of the bacterial cell suspension was added to each tube. Then, the tube was filled with 0.1-mm zirconium beads supplied by the manufacturer of the Mini-Beadbeater. The tubes were inserted into the arms of the Mini-Beadbeater in the same fashion as the 2-ml vials made for use with the machine. The conical tubes have the advantage of being transferrable to an Eppendorf centrifuge after mulling (by shaking back and forth) for 3 min in the Mini-Beadbeater. Tubes containing the disrupted cells, the phenol, and about 500 µl of the zirconium beads were spun for 15 min at 8,000×g, after which the aqueous layer (containing the nucleic acids) was removed.

Separation and Purification of DNA

Procedures analogous to G. Darby et al., 103 J. Bact. 159–165 (1970) were used to further purify the DNA in the aqueous layer. The aqueous phase, approximately 500 ul, was shaken with an equal volume of chloroform-isoamyl alcoholphenol (24:1:25) for 25 min. The aqueous phase was again recovered by centrifugation and ether extracted four to six times (each time retaining the aqueous phase). The DNA in the aqueous phase was then precipitated in 3 volumes of chilled ethanol. DNA thus obtained was suspended in and treated with RNase (Sigma Chemical Co., St. Louis, Mo.) at 50 ug/ml.

Aliquots of DNA which were subsequently used for homology studies were further processed to remove polysaccharides bound to mycobacterial DNA. A 5% solution of cetyltrimethylammonium bromide was added in a ratio of 200 ul/500 ul of DNA solution, and the mixture was allowed to incubate for 15 min at room temperature. See E. Hill et al., 112 J. Bact. 1033–1039

(1972) for analogous procedures. A few additional drops of cetyltrimethylammonium bromide were added to ensure that all the DNA was precipitated. The tubes were spun at 8,000×g for 15 min. The DNA pellet was washed with 0.4 M NaCl, suspended in 1 M NaCl, and extracted with 1 volume of chloroform-isoamyl alcohol (24:1). Chloroform-isoamyl alcohol extraction was repeated until there was no intermediate layer between the chloroform-isoamyl alcohol and the DNA-containing aqueous layer. The DNA was precipitated in 3 volumes of ethanol.

This procedure, which combines the phenol extraction with the physical rupture of the mycobacterial cells, produces DNA of high purity, with the DNA having an average molecular size of approximately 10 kilobases.

Fecal Samples 1 g of a *M. paratuberculosis* cell paste containing $10^{12}$ cells was mixed thoroughly with 4 g of bovine fecal material ($10^{11}$ *M. paratuberculosis* cells per g of fecal material). The fecal material was vortexed in 20 ml of TE buffer (pH 8.0) and allowed to settle for 1 hour. A 100-$\mu$l sample of the supernatant was added to a conical microcentrifuge tube. Of the 100 $\mu$l of supernatant, 10 $\mu$l was mixed in a second tube with 90 $\mu$l of fecal supernatant to which no mycobacterial cells had been added, and 10 $\mu$l of the material from the second tube was added to a third tube containing 90 $\mu$l of unadulterated fecal supernatant. This procedure was repeated to yield a series of 10-fold dilutions of *M. paratuberculosis* cells in bovine fecal supernatants. After being mulled in the Mini-Beadbeater for 3 min with phenol and about 500)l of the 0.1-mm zirconium beads, and further DNA purification as described above, the DNA pellets were suspended in 100 )l of TE buffer, 25 )l of which was used in the hybridization reaction. When tried by applicants, three to four times more DNA is harvested by this technique as opposed to Ribi pressure cell technique.

Hybridization

To test the DNA from the fecal sample using the probe, one follows procedures analogous to those of S. Moseley et al., 145 J. Inf. Dis. 863–869 (1982); P. Rigby, 113 J. Mol. Biol. 237–251 (1977); E. Southern 98 J. Mol. Biol 503–517 (1975). Briefly, the DNA from the feces sample is blotted onto nitrocellulose and exposed to the labelled probe in 50% formamide in 65° C., overnight. Then, the nitrocellulose is overlaid with x/ray film for 24–48 hours to detect blots where the $^{32}$P labelled DNA probe hybridized to *M. paratuberculosis* DNA. X-ray film is then developed by standard photographic development methods to reveal blots where hybridization occurred.

It should be understood that while round beads are preferred, other small bead-like objects of a density greater than that of standard glass beads can be used in a bead beater system. Also, while DNA is the preferred nucleotide containing probe, other nucleotide variant probes (e.g. synthetic, RNA) may also prove useful.

We claim:

1. A polynucleotide fragment that will bind to *M. paratuberculosis*, but not *M. bovis*, *M. phlei*, or *M. scrofulaceum* in a hybridization test under stringent conditions.

2. The fragment of claim 1, wherein the fragment is DNA.

3. The DNA fragment of claim 2, wherein the fragment is labelled with an indicator.

4. The DNA fragment of claim 2, wherein the fragment contains a DNA sequence identical to the one present in the *M. paratuberculosis* DNA fragment deposited as ATCC 40380.

* * * * *